United States Patent [19]

Bade et al.

[11] Patent Number: 6,150,550
[45] Date of Patent: Nov. 21, 2000

[54] PROCESS FOR PREPARING ALKOXYSILANES

[75] Inventors: Stefan Bade, Haltern; Udo Robers, Stadtlohn, both of Germany

[73] Assignee: Huels Aktiengesellschaft, Marl, Germany

[21] Appl. No.: 09/210,735

[22] Filed: Dec. 15, 1998

[30] Foreign Application Priority Data

Dec. 15, 1997 [DE] Germany ............ 197 55 597

[51] Int. Cl.⁷ .................... C07F 7/08; C07F 7/18
[52] U.S. Cl. ............................................. 556/471
[58] Field of Search ................................ 556/471

[56] References Cited

U.S. PATENT DOCUMENTS

| | | |
|---|---|---|
| 3,008,975 | 11/1961 | Schubert . |
| 4,173,576 | 11/1979 | Seiler et al. ............ 556/471 |
| 4,298,753 | 11/1981 | Schinabeck et al. . |
| 4,642,363 | 2/1987 | Groh et al. ............ 556/471 |
| 4,851,558 | 7/1989 | Nishda et al. . |
| 5,493,044 | 2/1996 | Schwindeman ........ 556/471 |

FOREIGN PATENT DOCUMENTS

| | | |
|---|---|---|
| 862 895 | 1/1953 | Germany . |
| 913 769 | 6/1954 | Germany . |
| 31 751 | 10/1964 | Germany . |
| 20 33 373 | 4/1971 | Germany . |
| 20 61 189 | 6/1972 | Germany . |
| 24 03 731 | 8/1974 | Germany . |
| 24 09 731 | 9/1975 | Germany . |
| 25 32 887 | 7/1976 | Germany . |
| 27 44 726 | 4/1979 | Germany . |
| 28 00 017 | 7/1979 | Germany . |
| 32 36 628 | 4/1984 | Germany . |
| 38 01 618 | 7/1989 | Germany . |
| 674137 | 6/1952 | United Kingdom . |

Primary Examiner—Paul F. Shaver
Attorney, Agent, or Firm—Oblon, Spivak, McClelland, Maier & Neustadt, P.C.

[57] ABSTRACT

A process for preparing alkoxysilanes by reacting alcohols with halosilanes which are dissolved in a nonpolar solvent that is immiscible with the alcohol.

22 Claims, 2 Drawing Sheets

PROCESS FOR PREPARING ALKOXYSILANES

BACKGROUND OF THE INVENTION

1. Field of the Invention

The present invention relates to an improved process for preparing alkoxysilanes from halosilanes and alcohols.

2. Discussion of the Background

Alkoxysilanes, e.g., of the formula I below, are important industrial intermediates or end products in organosilane chemistry. They are used, inter alia, as coupling agents in composite materials, for example in the coatings and glass fiber industry, in the foundry and in the manufacture of adhesives, and for the manufacture of elastomers. Individual examples which can be mentioned are silanized glass fibers, polymer systems or silicone systems reinforced by fine materials, e.g., permanently flexible sealants, silica-filled rubber articles, e.g. tires, the modification of hydroxy-functional surfaces, the silane polycondensation to give polyorganosiloxanes and preservatives for buildings and other structures.

The alkoxysilanes are prepared by reacting halosilanes, which can contain one or more halogen atoms, with an alcohol, for example an alkanol or an alkoxyalkanol, in accordance with the general equation below:

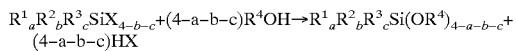

$$R^1_a R^2_b R^3_c SiX_{4-b-c} + (4-a-b-c)R^4OH \rightarrow R^1_a R^2_b R^3_c Si(OR^4)_{4-a-b-c} + (4-a-b-c)HX$$

In the formulae, $R^1$, $R^2$, $R^3$, $R^4$ and X, a, b and c, have the meaning specified below. As a by-product, the stoichiometric amount of hydrogen halide HX is therefore always formed.

The halosilanes are reacted with the alcohol either batchwise or continuously, the hydrogen halide formed being converted into the gas phase or remaining bound in the liquid phase. Customary techniques for removing the hydrogen halide by conversion into the gas phase are stripping, distillation (also reactive distillation). Processes of this type are described, inter alia, in DE 20 61 189 and U.S. Pat. No. 4,298,753 (continuous reactive distillation); DE 28 00 017, DE-A 38 01 618, DE-A 24 09 731 and DE-A 27 44 726 (distillation of the crude product to remove hydrogen chloride); DE-A 32 36 628 (connecting stirred tank and column in series); DE 862 895 and DD 31 751 (stripping of hydrogen chloride by inert gas). Considerable disadvantages of these processes for removing hydrogen halide by conversion into the gas phase are the secondary reactions of the hydrogen halide with the alkoxysilanes produced to form siloxanes according to the reaction equation:

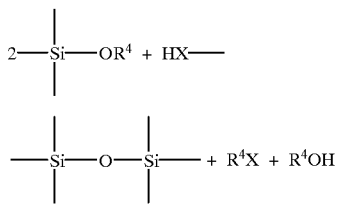

and the limitation of the degree of conversion of the halosilanes to alkoxysilanes by the thermodynamic equilibrium owing to the presence of hydrogen halide in the reaction mixture. This applies particularly if more than one halogen atom is to be replaced by an alkoxy radical. In this case, non-alkoxylated, mono- and polyalkoxylated silanes are present simultaneously when trihalosilanes are reacted with alcohol, the equilibrium constants decrease from the first to the third stage. That is to say that the third alkoxy group especially is difficult to introduce or that introduced third alkoxy groups readily react with hydrogen halide to reform a halosilane structure.

A sought-after alkoxysilane is (3-chloropropyl) methyldimethoxysilane (CPMDMO), which is formed from (3-chloropropyl)methyldichlorosilane and methanol. In this case also, the reaction product of the first stage, the monoalkoxychlorosilane, is favored over the dialkoxysilane. This is shown by comparing the equilibrium constants, that for the first stage at room temperature being considerably greater than 1, but that for the second stage being only 0.4. In a known process the reaction is carried out batchwise in a stirred-tank reactor, and the resulting hydrogen halide is removed from the reaction mixture by distillation. The yield is about 60%. It can be increased to 65% by adding methanolic sodium methoxide solution, but with the disadvantage that sodium chloride is produced and the risk that a 3-methoxypropyl group will result from the 3-chloropropyl group in a Williamson synthesis.

The disadvantages of the processes in which the hydrogen halide formed is converted into the gas phase are particularly serious because the transfer of the hydrogen halide from the liquid phase to the gas phase proceeds relatively slowly and thus the mass transport of the hydrogen halide has a critical effect on the entire process. The equilibrium is therefore shifted only comparatively slowly in favor of the wanted alkoxylated products, and the hydrogen halide promotes the formation of siloxanes, in accordance with the above equation. The hydrogen halide is particularly slowly converted to the gas phase in reactions with methanol, since it is readily soluble in methanol. Owing to the slow transfer of the hydrogen halide to the gas phase, the yields of alkoxysilane are decreased.

Another technique for removing the resulting hydrogen halide from the reaction mixture, which has already been motioned in connection with the synthesis of(3-chloropropyl)-methyldimethoxysilane, is binding the hydrogen halide in the liquid phase by reaction with basic substances. However, if acid-binding agents are used, e.g. ammonia or (tertiary) amines (DE 913 769, which describes the removal of hydrogen chloride by ammonia), or if alkoxides are used, stoichiometric amounts of salt are produced which need to be separated off from the product.

The use of solvents in the removal of hydrogen halide is likewise described. In this case the solvents serve to decrease the viscosity of the reaction mixture, which is always a single phase (DE-A 20 61 189), or to depress the boiling point of the reaction mixture, which is always a single phase (DE-A 28 00 017, DE-A 32 36 628). In contrast, the use of solvents in a two-phase reaction mixture has not yet been described.

In contrast, it is known that it is advantageous to select a reaction temperature <100° C. when the halosilane is reacted with the alcohol, to avoid unwanted side reactions to form siloxanes (DE-A 24 03 731). This requires hydrogen halide to be removed at the lowest possible temperature, although higher temperatures would be more favorable for this removal.

For the preparation of alkoxysilanes, the use of various reactors is described, that is to say stirred tanks (e.g. GB 674 137), tubular reactors—(DE-A 20 33 373), stirred tanks equipped with a column (e.g. —DE-A 32 36 328) and reaction-distillation columns (e.g., U.S. Pat. No. 4,298,753).

OBJECTS OF THE INVENTION

It is an object of the present invention to provide a process for preparing alkoxysilanes which is successful without salt formation by bases, but, nevertheless, effectively and rapidly removes the hydrogen halide from the reaction mixture, and, by this means avoids, or at least suppresses to a greater extent than was possible hitherto, the disadvantages of the processes described above, where the hydrogen halide is converted to the gas phase.

SUMMARY OF THE INVENTION

The object of the present invention, and others, is accomplished with a process for preparing alkoxysilanes of the general formula $$R^1_a R^2_b R^3_c Si(OR^4)_{4-a-b-c} \quad (I)$$

where
- $R^1$ is hydrogen, alkyl, alkenyl, aryl or haloalkyl;
- $R^2$ is hydrogen or alkyl;
- $R^3$ is hydrogen or alkyl; and
- $R^4$ is alkyl or alkoxyalkyl;
- a, b and c are identical or different and can be 0, 1, 2 or 3, with the proviso that $a+b+c \leq 3$, by reacting halosilanes of the general formula $$R^1_a R^2_b R^3_c SiX_{4-a-b-c} \quad (II)$$

where $R^1$, $R^2$ and $R^3$ and a, b, and c are as defined above, and X is fluorine chlorine, bromine or iodine, with an alcohol of the general formula $$R^4OH \quad (III)$$

where $R^4$ is as defined above
by dissolving the halosilane II in a nonpolar solvent which is immiscible with the alcohol III and bringing the solution into contact with the alcohol III.

A more complete appreciation of the invention and many of the attendant advantages thereof will be readily obtained as the same becomes better understood by reference to the following detailed description when considered in connection with the accompanying drawings.

DETAILED DESCRIPTION OF THE INVENTION

Figure 1:
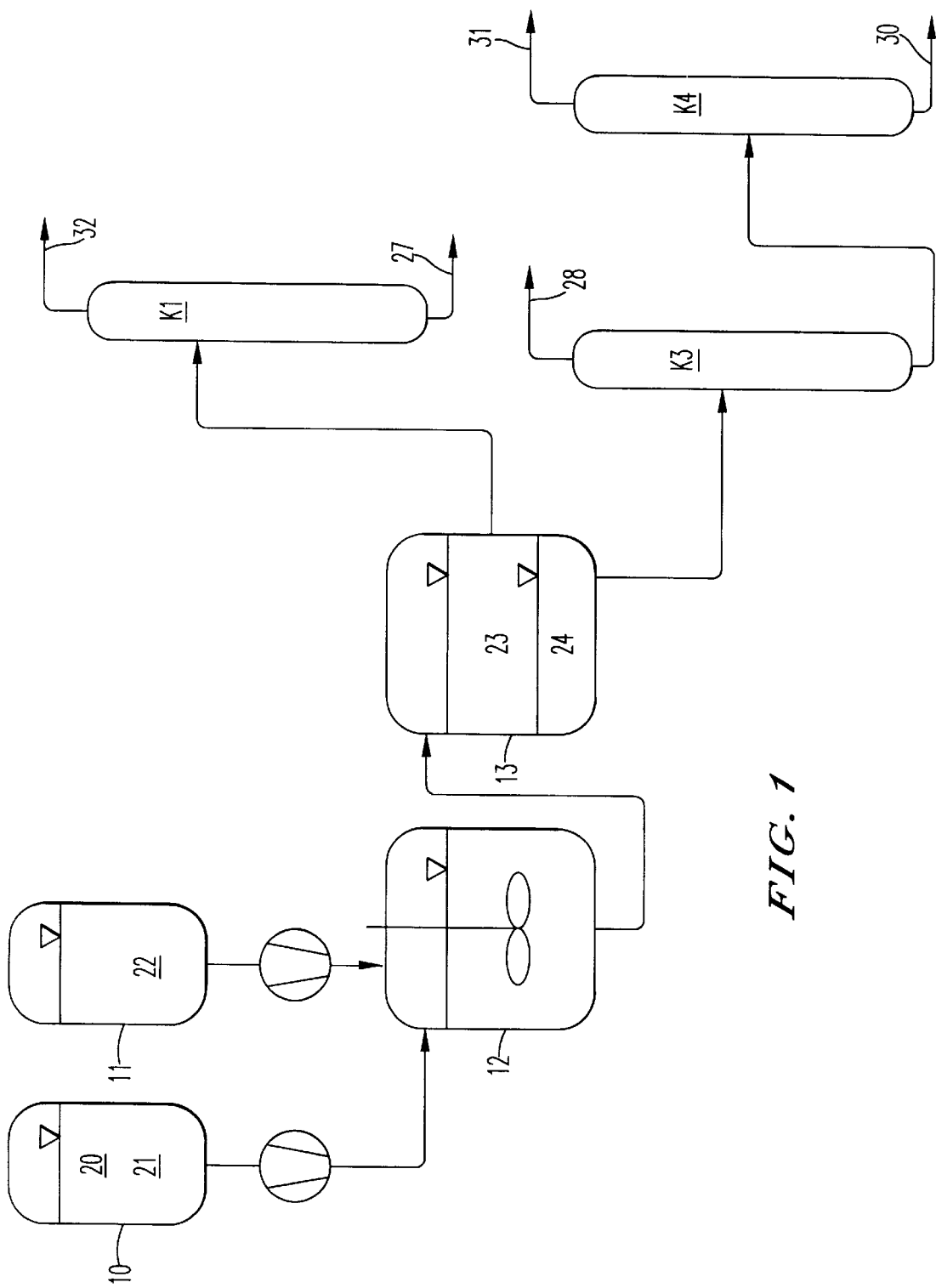
FIG. 1 is a block diagram of a plant for carrying out the process according to the invention batchwise.

The reaction to produce the alkoxysilanes may be termed a reactive extraction, since. simultaneously with the chemical reaction of the halosilane II with the alcohol III, a reaction product, namely the hydrogen halide being formed, is extracted into one of the phases, namely the alcohol phase.

The process according to the invention is associated with a number of surprising advantages. The reaction takes place at the interface of the two separate phases of the reaction mixture, the resulting alkoxysilane very largely remains in the nonpolar phase and thereby avoids contact with the hydrogen halide which is dissolved in the polar alcohol phase. Since the nonpolar phase is virtually free from hydrogen halide, on the one hand, the secondary reaction of the alkoxysilane to form siloxanes which are higher boiling or can no longer be distilled is virtually completely prevented and, on the other hand, the equilibrium of the alkoxylation reaction is shifted towards the alkoxysilanes or, in the case of halosilanes having more than one halogen atom, in the direction of the completely alkoxylated silanes. Furthermore, there is no conversion of haloalkyl substituents $R^1$ into alkoxyalkyl radicals.

The process proceeds at low temperatures, which contributes to suppressing the unwanted secondary reactions. Especially, higher-boiling alcohols need not be vaporized, as is the case in the reactive distillation. The process according to the invention is independent of the boiling positions of the chlorosilanes II, the alcohols III and the alkoxysilanes I. As a result, the reaction can generally be carried out at atmospheric pressure.

A desired result of the reactive extraction according to the invention is an improved selectivity of the formation of the (completely alkoxylated) alkoxysilane and thus a higher yield, which can considerably exceed 90% when the process is carried out continuously. If halosilanes having more than one halogen atom are used, all halogen atoms are replaced by alkoxy groups. This facilitates the work-up of the nonpolar phase (and improves the yield), because no incompletely alkoxylated products need to be removed. The polar alcohol phase can be worked up in a simple manner by distillation. If appropriate, the alkoxysilanes, which are present in the alcohol phase in accordance with the distribution equilibrium, can be extracted with fresh nonpolar solvent before the distillation and recycled to the reaction. The hydrogen halide removed is highly pure. It can be used directly for many purposes and does not need to be disposed of by neutralization with salt formation.

In preferred alkoxysilanes 1, and thus also in preferred halosilanes II and alcohols III,
- $R^1$ is an alkyl, alkenyl or haloalkyl radical having 1 to 6 carbon atoms (and, e.g., 1 to 3, or more, halogen atoms) or an aryl radical having 6 to 10 carbon atoms;
- $R^2$ and $R^3$ independently of one another are hydrogen or alkyl radicals having 1 to 6 carbon atoms;
- $R^4$ is an alkyl radical having 1 to 6, in particular 1 or 2, carbon atoms or an alkoxyalkyl radical having 3 to 8 carbon atoms and 1 or 2 oxygen atoms; and X is chlorine or fluorine.

Of the alkyl radicals which can be present in the preferred alkoxysilanes I and the preferred starting materials II and III, mention may be made of methyl, ethyl, 1-propyl, 2-propyl, 1-butyl, 2-butyl, 2-methyl-2-propyl, 1-pentyl and 1-hexyl. Preferred alkenyl radicals are, for example, vinyl, 1- and 2-propenyl, 1-butenyl and 5-hexenyl. Examples of preferred haloalkyl radicals are chloromethyl, 2-chloroethyl, 3-chloropropyl and 3,3,3-trifluoropropyl. The preferred aryl radicals include phenyl, tolyl, styryl, 1-naphthyl and benzyl. Of the preferred alkoxyalkyl radicals, mention may be made of, for example, 2-methoxyethyl and 2-(2'-methoxyethyl) ethyl.

As preferred halosilanes II to be reacted, mention may be made of, for example, trichlorosilane, methyltrichlorosilane, dimethyldichlorosilane, trimethylchlorosilane, diethyldichlorosilane, (3-chloropropyl)trichlorosilane, (3-chloropropyl)methyldichlorosilane, (3,3,3-trifluoropropyl)methyldichlorosilane, vinyltrichlorosilane, propyltrichlorosilane, isobutyltrichlorosilane and n-octyltrichlorosilane.

Examples of preferred suitable alcohols III are methanol, ethanol, 1-propanol, 2-propanol, 1-butanol, 1-hexanol and 2-methoxyethanol (or methyl glycol) and 2-ethoxyethanol (or ethyl glycol). The alcohol may contain, for example, 1 to 10 carbon atoms, inclusive of all specific values and subranges therebetween, and 0, 1, 2, 3 (or more) oxygen atoms in addition to the oxygen atom of the hydroxyl group.

The alcohol III is expediently used in a considerable stoichiometric excess, preferably a 1- to 10-fold stoichiometric excess, in relation to the halosilane so that it is able to dissolve the hydrogen halide being released. This stoichiometric excess of the alcohol includes all specific values and subranges therebetween, such as 2-, 5-, 6-, 7-, 8- and 9-fold stoichiometric excess.

The nonpolar solvent for the halosilanes II and, after the reaction, the alkoxysilanes I must not be miscible with the (polar) alcohol III. Advantageously, the nonpolar solvent is chosen in such a manner that the alcohol III is not dissolved by more than 10%, advantageously not by more than 5%, at 20° C., and, conversely, the alcohol III dissolves the nonpolar solvent only to a corresponding extent. The dielectric constant of the solvent is generally >10. Suitable solvents are, for example, liquid aliphatic or cycloaliphatic hydrocarbons having 5 to 16 carbon atoms, such as pentane, hexane, octane, dodecane and isomers of these hydrocarbons and mixtures of these hydrocarbons and/or their isomers; and aromatic hydrocarbons having 6 to 8 carbon atoms, such as benzene, toluene, the isomeric xylenes and halogenated aliphatic hydrocarbons having 1 to 8 carbon atoms, such as dichloromethane, chloroform and carbon tetrachloride.

The nonpolar solvent is expediently used in such an amount that the content of the halosilanes and/or alkoxysilanes dissolved therein is 5 to 30, preferably 10 to 20, percent by weight. These weight percent ranges include all specific values and subranges therebetween. such as 8, 12, 15 and 25% by weight.

The reaction according to the invention proceeds, as mentioned, at low temperatures. Expediently, −20 to +60° C., in particular 10 to 30° C., is employed. These temperature ranges include all specific values and subranges therebetween, such as −10, 0, 5, 15 20, 25, 40 and 50° C.

The yield of the alkoxysilane may be at least 25%, at least 50%, at least 75%, at least 85%, at least 90%, at least 95%, at least 97% and at least 99%, up to 100%, based on the halosilane, inclusive of all specific values and subranges there between.

FIG. 1 is a block diagram of a plant for carrying out the process according to the invention batchwise. From the vessel 10, the halosilane 20 is charged, together with the solvent 21 and, from the vessel 11, the alcohol 22, into the mixing vessel 12, e.g. a stirred tank, in which the two liquid phases are mixed with one another. The temperature increases in the course of this to 20 to 60° C., depending on the amounts of substances used. The temperature can be controlled by feeding the halosilane 20 and the alcohol 22 into the stirred tank 12 gradually. Alternatively, the stirred tank can have a jacket for the passage of a heat exchange liquid or an attached reflux condenser, so that the boiling point of the solvent determines the reaction temperature.

The reaction is generally terminated after 10 minutes to 100 minutes, and the reaction mixture is transferred to the separation vessel 13, in which the lighter nonpolar product phase 23 and the heavier alcohol phase 24 separate. The latter is introduced into the column K3 and is there separated into hydrogen halide 28 and a bottom fraction which is itself fractionated in the column K4 into a top fraction 31, which comprises the alcohol and silanes and can be introduced into a new batch, and a bottom fraction 30 which comprises high-boilers (siloxanes) and can be discarded, for example combusted.

The nonpolar product phase 23 is distilled in the column K1. This produces the top product 32 which comprises the reaction product alkoxysilane together with the solvent and small amounts of alcohol and can be separated in a further distillation. Alternatively, it is also possible to take off the alkoxysilane in the column K1 as a side stream and the solvent and the alcohol as overhead stream. The bottom fraction 27 again comprises highboilers (siloxanes) and can be treated in a similar manner to the bottom fraction 30.

Figure 2:
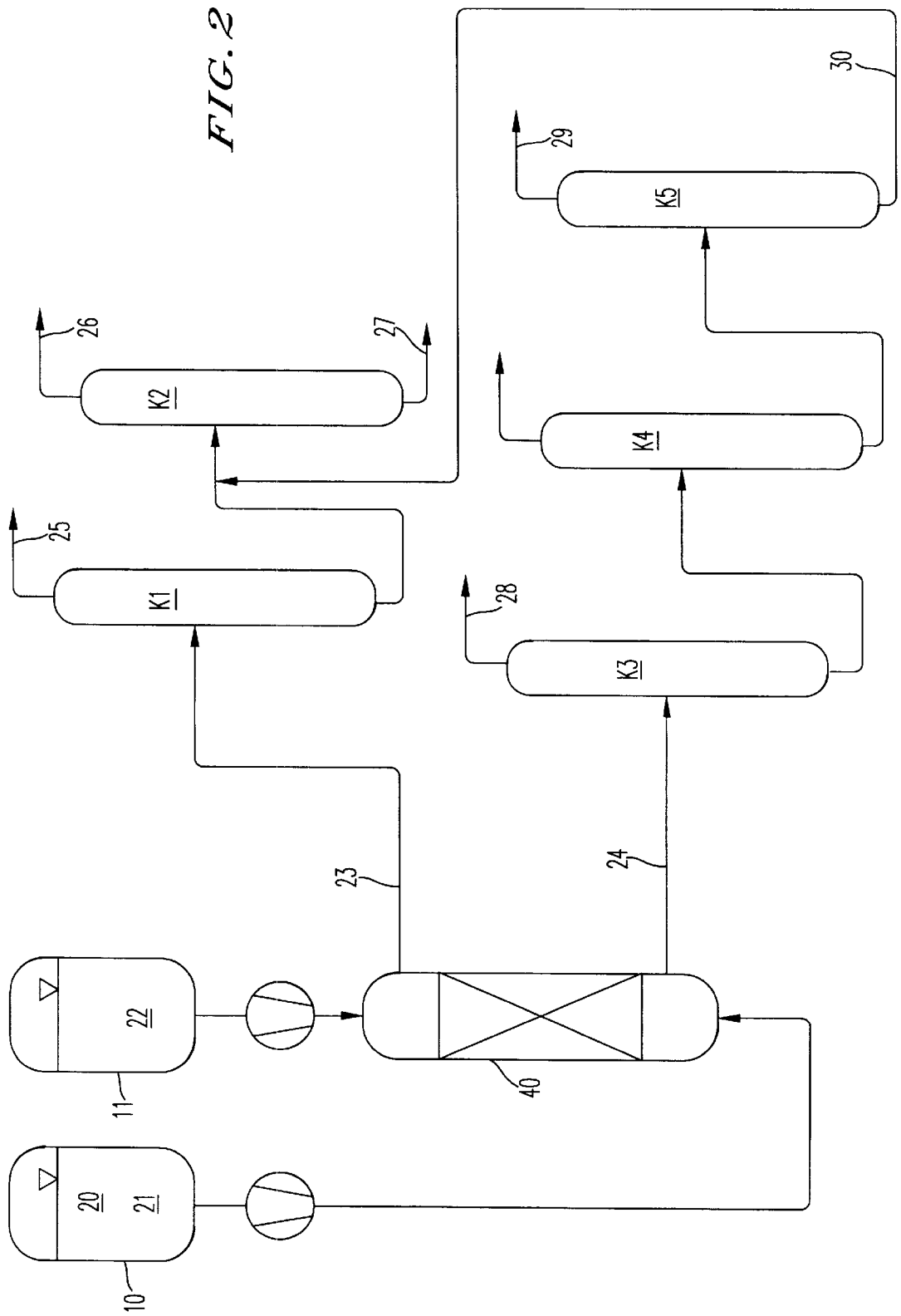
FIG. 2 is a block diagram of a plant in which the process according to the invention can be carried out continuously.

FIG. 2 is the block diagram of a plant for carrying out the process according to the invention continuously. From the vessel 10, the chlorosilane 20, dissolved in the nonpolar solvent 21, is continuously introduced as lighter phase into the bottom part of the reaction-extraction column 40. From the vessel 11 the alcohol 22 is continuously applied as denser phase to the top of the reaction-extraction column 40, in which it moves downwards as a continuous phase in countercurrent to the ascending lighter nonpolar phase which is dispersed in the denser phase. A homogeneous dispersion can be achieved by means of suitable internals or packings of the reaction-extraction column 40 or, particularly advantageously, by pulsation. The nonpolar lighter phase 23 is taken off as overhead product and the denser polar alcohol phase as bottom product 24.

Both the nonpolar phase 23 and the polar alcohol phase 24 are continuously worked up in columns. From the nonpolar phase 23, the nonpolar solvent is firstly distilled off together with small amounts of alcohol in the column K1 and can be recycled as stream 25 to the vessel 10. The bottom product of column K1 is passed into column K2, from which the product 26, that is the (completely) alkoxylated alkoxysilane, is taken off as overhead product and the high-boilers 27 are taken off as bottom product.

The polar phase 24 is first freed from hydrogen halide 28 in the column K3, and in the column K4, alcohol 22 is removed as overhead product, which can be recycled to the vessel 11. The bottom product of the column K4 is passed into the column K5 in which partially alkoxylated chlorosilane 29 is taken off as overhead product and can be recycled to the vessel 10, while high-boilers 30 are passed into the column K2, in which they are ejected from the process, after removing distillable portions, as a part of the high-boilers 27. When monohalosilanes are used as starting materials, no partially alkoxylated silanes are formed. The column K5 can then be omitted and the bottom product of the column K4 is introduced directly into the column K2.

EXAMPLES

Having generally described this invention, a further understanding can be obtained by reference to certain specific examples which are provided herein for purposes of illustration only and are not intended to be limiting unless otherwise specified.

Example 1

Batchwise preparation of (3-chloro-propyl)methyldimethoxysilane (CPMDMO)

600 g of a solution of 60 g of (3-chloropropyl)methyldichlorosilane (CPMDCS) in 540 g of cyclohexane are placed into a stirred tank. 110 g of methanol are then added, and the two phases are intensively mixed with one another. The reaction is performed at room temperature for 30 minutes. The two phases are then separated by settling. The denser methanol phase comprises the majority of the hydrogen chloride formed and smaller amounts of CPMDMO and the only mono-alkoxylated (3-chloropropyl)methylchloromethoxysilane (CPMCMO). The tighter cyclohexane phase comprises the majority of the product CPMDMO formed, while the monoalkoxylated CPMCMO is not present in the cyclohexane phase. Table 1 below gives the composition of the two phases as determined by gas chromatography.

TABLE 1

|  | Cyclohexane phase | Methanol phase |
|---|---|---|
| Starting materials | 540 g of cyclohexane | 110 g of methanol |
|  | 60 g of CPMDCS |  |
| Result | 48.9 g of CPMDMO | 2.57 g of CPMDMO |
|  | 0 g of CPMCMO | 0.62 g of CPMCMO |
|  | 4.47 g of high-boilers | 22.82 g of HCl |
|  | 540 g of cyclohexane | 89.94 g of methanol |
| Yield of CPMDMO |  | 90% |
| Yield of CPMCMO |  | 1.05% |
| Yield of high-boilers |  | 8.95% |

Example 2

Continuous preparation of (3-chloropropyl) methyldimethoxysilane (CPMDMO)

Methanol is fed in at the top of a continuously operated reaction-extraction column and CPMDCS in cyclohexane is fed in at the bottom. The nonpolar phase is the continuous phase; the alcohol is dispersed in the nonpolar phase at the top of the column using a ring distributor. The CPMDMO-laden cyclohexane phase is taken off at the top of the reaction-extraction column, and the hydrogen chloride-laden alcohol phase is taken off at the bottom of the reaction-extraction column. Both phases are analyzed by means of gas chromatography, Table 2 below shows the streams in g/h, differentiated into feed and output streams and into polar and nonpolar phases

TABLE 2

|  | Feed | | Output | |
|---|---|---|---|---|
|  | Polar | Nonpolar | Polar | Nonpolar |
| Cyclohexane | 0 | 900 | 22.0 | 878 |
| Methanol | 279 | 0 | 241.0 | 4.8 |
| CMPDCS | 0 | 100 | 0 | 0 |
| CPMCMO | 0 | 0 | 1.7 | 0 |
| CPMDMO | 0 | 0 | 3.8 | 87.0 |
| Siloxane | 0 | 0 | 1.9 | 0 |
| HCl | 0 | 0 | 37.3 | 0 |
| Total | 279 | 1000 | 307.7 | 970.6 |

The yield of CPMDMO in the two phases is 96%, based on CPMDCS used (and at the same time reacted). CPMCMO (yield 1.7%) is only present in the alcohol phase, and siloxane (yield 2.3%) only in the cyclohexane phase.

Obviously, numerous modifications and variations of the present invention are possible in light of the above teachings. It is therefore to be understood that within the scope of the appended claims, the invention may be practiced otherwise than as specifically described herein.

The present application is based on German Patent Application No. 197 55 597.7, filed Dec. 15, 1997, and incorporated herein by reference in its entirety.

What is claimed is:

1. A process for preparing an alkoxysilane of formula (I):

wherein $R^1$ is a hydrogen atom, an alkyl radical, an alkenyl radical, an aryl radical or a haloalkyl radical; $R^2$ is a hydrogen atom or an alkyl radical; $R^3$ is a hydrogen atom or an alkyl radical; $R^4$ is an alkyl radical or an alkoxyalkyl radical; and a, b and c are each, independently, 0, 1, 2 or 3 with the proviso that $a+b+c \leq 3$, comprising:

forming a two phase liquid reaction medium of an alcohol of formula (III):

wherein $R^4$ is as defined above, with a halosilane of formula (II):

wherein X is fluorine, chlorine, bromine or iodine, dissolved in a nonpolar solvent that is immiscible with the alcohol, wherein the amount of alcohol of the alcohol phase is at least one fold stoichiometric excess in relation to said halosilane; and commencing the reaction between the alcohol of the alcohol phase with the halosilane in the nonpolar solvent phase, with the hydrogen halide product produced being removed from contact with the nonpolar solvent phase in which it is formed by dissolution into the alcohol phase.

2. The process of claim 1, wherein $R^1$ is an alkyl, alkenyl or haloalkyl radical having 1 to 6 carbon atoms, or an aryl radical having 6 to 10 carbon atoms;

$R^2$ and $R^3$ are each, independently, a hydrogen atom or an alkyl radical having 1 to 6 carbon atoms;

$R^4$ is an alkyl radical having 1 to 6 carbon atoms, or an alkoxyalkyl radical having 3 to 8 carbon atoms and 1 or 2 oxygen atoms; and X is chlorine or fluorine.

3. The process of claim 1, wherein the halosilane is (3-chloropropyl)methyldichlorosilane and the alcohol is methanol or ethanol.

4. The process of claim 1, wherein the alcohol is used in a 1- to 10-fold stoichiometric excess in relation to the halosilane.

5. The process of claim 1, wherein the nonpolar solvent is a liquid aliphatic or cycloaliphatic hydrocarbon having 5 to 16 carbon atoms, an aromatic hydrocarbon having 6 to 8 carbon atoms, or a halogenated aliphatic hydrocarbon having 1 to 8 carbon atoms.

6. The process of claim 1, wherein the nonpolar solvent is used in such an amount that the content of the halosilanes and/or alkoxysilanes dissolved therein is 5 to 30 percent by weight.

7. The process of claim 1, which is conducted at −20 to +60° C.

8. The process of claim 1, which is conducted batchwise using a mixing tank and a settling tank.

9. The process of claim 1, which is carried out continuously in a reaction-extraction column in which the alcohol phase and the solvent phase are conducted in countercurrent.

10. The process of claim 1, wherein the halosilane is selected from the group consisting of trichlorosilane, methyltrichlorosilane, dimethyldichlorosilane, trimethylchlorosilane, diethyldichlorosilane, (3-chloropropyl)trichlorosilane, (3-chloropropyl) methyldichlorosilane, (3,3,3-trifluoropropyl) methyldichlorosilane, vinyltrichlorosilane, propyltrichlorosilane, isobutyltrichlorosilane and n-octyltrichlorosilane.

11. The process of claim 1, wherein the alcohol represented by formula (III) has 1 to 10 carbon atoms 0, 1, 2, 3 oxygen atoms in addition to the oxygen atom of the hydroxy group.

12. The process of claim 11, wherein the alcohol represented by formula (III) is selected from the group consisting of methanol, ethanol, 1-propanol, 2-propanol, 1-butanol, 1-hexanol and 2-methoxyethanol and 2-ethoxyethanol.

13. The process of claim 1, wherein said stoichiometric excess of the alcohol to halosilane is an at least two fold excess.

14. The process of claim 1, wherein the alcohol is not dissolved by more than 10% by weight in the nonpolar solvent at 20° C.

15. The process of claim 1, wherein the nonpolar solvent comprises at least one member selected from the group consisting of pentane, hexane, octane, dodecane, benzene, toluene, the isomeric xylenes, dichloromethane, chloroform and carbon tetrachloride.

16. The process of claim 1, wherein
   $R^1$ is an alkyl, alkenyl or haloalkyl radical having 1 to 6 carbon atoms, or an aryl radical having 6 to 10 carbon atoms;
   $R^2$ and $R^3$ are each, independently, a hydrogen atom or an alkyl radical having 1 to 6 carbon atoms;
   $R^4$ is an alkyl radical having 1 to 6 carbon atoms, or an alkoxyalkyl radical having 3 to 8 carbon atoms and 1 or 2 oxygen atoms; and
   X is chlorine or fluorine; and
   the nonpolar solvent is a liquid aliphatic or cycloaliphatic hydrocarbon having 5 to 16 carbon atoms, an aromatic hydrocarbon having 6 to 8 carbon atoms, or a halogenated aliphatic hydrocarbon having 1 to 8 carbon atoms.

17. The process of claim 16, wherein the nonpolar solvent comprises at least one member selected from the group consisting of pentane, hexane, octane, dodecane, benzene, toluene, the isomeric xylenes, dichloromethane, chloroform and carbon tetrachloride.

18. The process of claim 17, wherein the alcohol comprises methanol or ethanol.

19. The process of claim 18, further comprising isolating the alkoxysilane from the reaction mixture.

20. The process of claim 19, wherein the alkoxysilane is produced in a yield of at least 90% based on the halosilane.

21. The process of claim 1, further comprising isolating the alkoxysilane from the reaction mixture.

22. The process of claim 21, wherein the alkoxysilane is produced in a yield of at least 90% based on the halosilane.

* * * * *